United States Patent [19]

Biedermann et al.

[11] Patent Number: 4,518,783
[45] Date of Patent: May 21, 1985

[54] PROCESS FOR PRODUCING (-)-2-[1-(2,6-DICHLOROPHENOXY)-ETHYL]-1,3-DIAZACYCLOPENT-2-ENE

[75] Inventors: Jürgen Biedermann, Pulheim-Stommeln; Gerrit Prop, Pulheim; Ille-Stephanie Doppelfeld, Bergheim-Glessen, all of Fed. Rep. of Germany

[73] Assignee: A. Nattermann & Cie GmbH, Cologne, Fed. Rep. of Germany

[21] Appl. No.: 498,786

[22] Filed: May 27, 1983

Related U.S. Application Data

[63] Continuation-in-part of Ser. No. 367,946, Apr. 13, 1982, abandoned.

[30] Foreign Application Priority Data

Dec. 10, 1981 [DE] Fed. Rep. of Germany ....... 3149009

[51] Int. Cl.$^3$ .......................................... C07D 233/22
[52] U.S. Cl. ................................................. 548/353
[58] Field of Search .................... 548/353; 424/273 R

[56] References Cited

U.S. PATENT DOCUMENTS 3,966,757  6/1976  Baganz et al. ..................... 548/353
4,025,639  5/1977  Baganz et al. ..................... 424/273

OTHER PUBLICATIONS

Karrer, *Organic Chemistry*, 2nd Ed., pp. 92–102, (1946).
March, J., *Advanced Organic Chemistry*, McGraw Hill, 1968, pp. 90–91 and 338.
*Chemical Abstracts*, 65:13531f, (1966), [Battaglino, G., *Ann. Chim.*, 56(7), 820–6, (1966)].
*Chemical Abstracts*, 71:49581v, (1969), [Stolze, F., et al., E. German, 64,723, 11/20/68].
Fieser, M., et al., *Reagents for Organic Synthesis*, vol. 4, Wiley-Interscience, New York, 1974, p. 508.

*Primary Examiner*—Richard A. Schwartz
*Attorney, Agent, or Firm*—Pearne, Gordon, Sessions, McCoy, Granger & Tilberry

[57] ABSTRACT

This invention relates to processes for producing the (-)-2-[1-(2,6-dichlorophenoxy)-ethyl]-1,3-diazacyclopent-2-ene and to pharmaceutically acceptable acid addition salts thereof and the method for lowering the blood pressure in human beings suffering from increased blood pressure, using these compounds.

2 Claims, No Drawings

PROCESS FOR PRODUCING (-)-2-[1-(2,6-DICHLOROPHENOXY)-ETHYL]-1,3-DIAZACYCLOPENT-2-ENE

This application is a continuation-in-part application of our copending application Ser. No. 367,946, filed Apr. 13, 1982, now abandoned.

This invention relates to processes for producing the (−)-2-[1-(2,6-dichlorophenoxy)-ethyl]-1,3-diazacyclopent-2-ene corresponding to formula I:

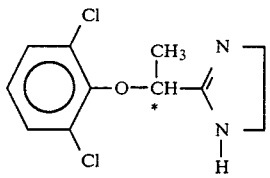

* = asymmetric centre and to the pharmaceutically acceptable acid additions salts thereof, and to the use thereof as active substance in pharmaceutical compositions, in particular for treating circulatory disorders, especially for controlling high blood pressure.

Processes for the production of the racemic compound (±)-2-[1-(2,6-dichlorophenoxy)-ethyl]-1,3-diazacyclopent-2-ene which is known as an anti-hypertonic, are described in U.S. Pat. Nos. 3,966,757 and 4,025,639.

Although it is known that 2-[1-(2,6-dichlorophenoxy)-ethyl]-1,3-diazacyclopenten-2-ene can exist in two optically active anantiomeric forms by virtue of the asymmetrically substituted carbon atom, the optically active levorotatory or dextrorotatory enantiomers have hitherto not been separated or produced.

Separation of the levorotatory enantiomers to elucidate the relation between optical activity and biological activity has been achieved by a known resolution method using levorotatory dibenzoyl tartaric acid.

Surprisingly, pharmacological tests have shown that only the levorotatory enantiomer causes a very pronouned, long-lasting fall in blood pressure, whereas the dextro-rotatory enantiomer has practically no effect in this model.

It has also been shown in a subsequent comparison of the pharmacological activity of the levorotatory enantiomer with the racemic compound that half the quantity of the levorotatory enantiomer is sufficient to achieve a reduction in blood pressure of the same level and duration.

The synthesis of the optically active compound according to the present invention is characterized in that it is based on optically active starting materials. Thus, for example, a (−)-2-hydroxypropionic acid-$C_{1-4}$ alkyl ester is reacted with excess thionylchloride in the presence of catalytic quantities of dimethylformamide with configuration reversal to produce a (+)-2-chloropropionic acid-$C_{1-4}$ alkyl ester. The subsequent etherification with 2,6-dichlorophenol takes place with another configuration reversal in suitable organic solvents, for example in acetonitrile, butanone or dimethylformamide, in the presence of a base, for example sodium hydride, alkalimethylate, alkaliethylate or 1,4-diazabicyclo-(2,2,2)-octane at a temperature in the range of from 60° to 150° C., preferably at 80° C., to produce a $C_{1-4}$ alkyl ester of (−)-2-(2,6-dichlorophenoxy)-propionic acid which, as well as functional acid derivatives thereof, is used as starting material for the synthesis of 1,3-diazacyclopentene derivatives. The reaction may be carried out with ethylene diamine itself or with a reactive N-derivative of ethylene diamine, or with ammonia or an ammonia-releasing agent together with a compount which may be converted into ethylene diamine by treating with ammonia. The following, for example, may be used as functional acid derivatives: $C_{1-4}$ alkylesters, acid halides, amides, thiamides, amidines, imido acid esters or the nitrile of 2-(2,6-dichlorophenoxy)-propionic acid.

In the present process, the (−)-2-(2,6-dichlorophenoxy)-propionic acid ethylester as above obtained is reacted with a large excess of 1,2-diaminoethane at room temperature and is converted into (−)-2-(2,6-dichlorophenoxy)-propionic acid-N-(2-aminoethyl)-amide which is dehydrated or cyclized with a titanium tetrachloride/tetrahydrofurane complex in chloroform in the presence of 4-dimethylaminopyridine at from 0° to 30° C. into (−)-2-[1-(2,6-dichlorophenoxy)-ethyl]-1,3-diazacyclopent-2-ene.

The levorotatory base is then converted into a physiologically acceptable acid addition salt using a suitable organic or inorganic acid in a lower alcohol. Thus, (−)-2-[1-(2,6-dichlorophenoxy)-ethyl]-1,3-diazacyclopent-2-ene hydrochloride is obtained from the (−)-base, for example using a propan-2-ol solution of hydrogen chloride.

In a variation of the present process, the (−)-2-(2,6-dichlorophenoxy)-propionic acid ethylester obtained as above described, is reacted with an ethanolic solution of ammonia at room temperature and is converted into (+)-2-(2,6-dichlorophenoxy)-propionic acid amide which is difficultly soluble in ethanol. This amide is dehydrated at from 0° to 30° C. with a titanium tetrachloride/tetrahydrofurane complex and 4-methyl-morpholine in chloroform into (−)-2-(2,6-dichlorophenoxy)-propionic acid nitrile. By introducing hydrogen chloride at 0° C., the nitrile is then converted with ethanol in chloroform into (−)-2-(2,6-dichlorophenoxy)-propionimido acid ethylester hydrochloride. This compound is dissolved in ethanol and is cyclized by adding 1,2-diaminoethane to produce (−)-2-[1-(2,6-dichlorophenoxy)-ethyl]-1,3-diazacyclopent-2-ene.

Analogously to the previous process, (−)-2-[1-(2,6-dichlorophenoxy)-ethyl]-1,3-diazacyclopent-2-ene hydrochloride is produced from the (−)-base thus obtained.

Many various pharmaceutically acceptable acid addition salts may be obtained from the compound according to the present invention in the form of a free base, by treating with suitable acids according to the conventional methods. The following, for example, are suitable for the production of such salts: inorganic acids, for example hydrobromic acid, sulphuric acid or phosphoric acid, or organic acids, for example acetic acid, glycollic acid, succinic acid, fumaric acid, malic acid, tartaric acid, citric acid, benzoic acid or cinnamic acid.

The compound according to the present invention and the pharmaceutically acceptable acid addition salts thereof have valuable pharmacological properties, in particular a strong blood pressure-reducing effect of long duration and with minor side effects. The reduction in the peripheral resistance is desirable to ease the heart in the case of high blood pressure and it renders the compounds of the present invention particularly suitable for treating circulatory disorders.

The present invention also relates to pharmaceutical preparations which contain the compound corresponding to formula I and prepared by the present process or contain pharmaceutically applicable acid addition salts of this compound. The pharmaceutical preparations according to the present invention are preparations for enteral, such as oral or rectal, and for parenteral administration, and contain the pharmacological active substance on its own or together with a conventional, pharmaceutically acceptable carrier. The pharmaceutical preparations containing the active substance are advantageously in the form of individual doses which correspond to the required method of administration, for example tablets, coated tablets, capsules, suppositories, granules, solutions, emulsions or suspensions. The dosage of the compound usually ranges from 0.05 to 50 mg per dose, preferably from 0.075 to 0.1 mg per dose and may be administered once or several times.

The production of the compounds according to the present invention is explained in more detail by the following Examples. The melting points which are specified in the Examples were measured using a Büchi 510 melting point apparatus and are specified in °C. and are uncorrected.

EXAMPLE 1

Synthesis of (−)-2-[1-(2,6-dichlorophenoxy)-ethyl]-1,3-diazacyclopent-2-ene hydrochloride (+)-2-chloropropionic acid ethylester 250 g ( 2.119 mols) of (−)-2-hydroxypropionic acid ethylester $[\alpha]_D^{20} = -11.0°$ (undiluted) are chlorinated with 264.0 g ( 2.218 mols) of thionylchloride in the presence of 1.5 ml of dimethylformamide at boiling temperature. 93.0 g of (+)-2-chloropropionic acid ethylester $C_5H_9ClO_2$ [136.6] are obtained, B.p.: 143° C. $[\alpha]_D^{20} = +19.8°$ (undiluted)

(−)-2-(2,6-dichlorophenoxy)-propionic acid ethylester 65.5 g ( 0.402 mols) of 2,6-dichlorophenol are heated to boiling point in 300 ml of butanone with 38.0 g ( 0.542 mols) of potassium ethylate and 76.0 g ( 0.556 mols) of (+)-2-chloropropionic acid ethylester for 48 hours, with stirring and under reflux. After working up, 62.0 g of (−)-2-(2,6-dichlorophenoxy)-propionic acid ethylester $C_{11}H_{12}Cl_2O_3$ [263.1] are obtained, Bp$_{0.3}$: 115°–117° C. $[\alpha]_D^{20} = -37.1°$ (undiluted)

(−)-2-(2,6-dichlorophenoxy)-propionic acid-N-(2-aminoethyl)-amide.

46.0 g ( 0.1748 mols) of (−)-2-(2,6-dichlorophenoxy)-propionic acid ethylester are stirred for 6 hours at room temperature with 212.0 g ( 3.527 mols) of 1,2-diaminoethane and, after working up, produce 38.0 g (−)-2-(2,6-dichlorophenoxy)-propionic acid-N-(2-aminoethyl)-amide, $C_{11}H_{14}Cl_2N_2O_2$ [277.2] as a high viscosity oil, $[\alpha]_D^{20} = -5.8°$ (c=1/ethanol)

(−)-2-[1-(2,6-dichlorophenoxy)-ethyl]-1,3-diazacyclopent-2-ene 58.6 ( 0.3089 mols) of titanium tetrachloride are dissolved in a mixture of 700 ml of absolute chloroform and 25 ml of tetrahydrofuran at 0° C. and are mixed with 35.0 g ( 0.1263 mols) of (−)-2-(2,6-dichlorophenoxy)-propionic acid-N-(2-aminoethyl)-amide. A solution of 74.0 g ( 0.6056 mols) of 4-dimethylaminopyridine is then added dropwise very slowly at 0° C. with stirring and the mixture is further stirred for 36 hours at room temperature after the solution has been added. After working up and after purification by column chromatography (silica gel-dry column, eluant: chloroform/tetrahydrofuran 3:1), 21.0 g of (−)-2-[1-(2,6-dichlorophenoxy)-ethyl]-1,3-diazacyclopent-2-ene $C_{11}H_{12}Cl_2N_2O$ [259.1], are obtained, Mp.: 126°–127° C.: $[\alpha]_D^{20} = -80.2°$ (c=1/ethanol).

(−)-2-[1-(2,6-dichlorophenoxy-ethyl]-1,3-diazacyclopent-2-ene hydrochloride 10.0 g of (−)-2-[1-(2,6-dichlorophenoxy)-ethyl]-1,3-diazacyclopent-2-ene are dissolved in 40 ml of propan-2-ol are are mixed with 40 ml of a saturated solution of hydrogen chloride in propan-2-ol. After a corresponding working-up operation, 7.8 g of (−)-2-[1-(2,6-dichlorophenoxy)-ethyl]-1,3-diazacyclopent-2-ene hydrochloride $C_{11}H_{12}Cl_2N_2O \cdot HCl$ [295.6] are obtained. Mp.: 229°–230° C. $[\alpha]_D^{20} = -33.2°$ (c=1/ethanol).

EXAMPLE 2

Synthesis of (−)-2-[1-(2,6-dichlorophenoxy)-ethyl]-1,3-diazacyclopent-2-ene hydrochloride The starting material is described in Example 1, stage 2.

(+)-2-(2,6-dichlorophenoxy)-propionic acid amide

Ammonia is introduced at room temperature and with stirring for 24 hours into a solution of 60 g ( 0.2281 mols) of (−)-2-(2,6-dichlorophenoxy)-propionic acid ethylester in 100 ml of ethanol saturated with ammonia. After working up, 41.0 g of (+)-2-(2,6-dichlorophenoxy)-propionic acid amide $C_9H_9Cl_2NO_2$ [234.1] are obtained, Mp.: 193° C. $[\alpha]_D^{20} = +20.1°$ (c=1/acetone)

(−)-2-(2,6-dichlorophenoxy)-propionitrile

A solution of 16.3 g ( 0.0859 mols) of titanium tetrachloride in 50 ml of absolute chloroform and 7 ml of tetrahydrofuran is mixed with 10.0 g ( 0.0427 mols) of (+)-2-(2,6-dichlorophenoxy)-propionic acid amide. A solution of 17.3 g ( 0.1709 mols) of 4-methylmorpholine is then added dropwise very slowly with stirring at 0° C. and after the solution has been added, the contents of the flask are further stirred for 24 hours at 30° C. After working up, 7.0 g of (−)-2-(2,6-dichlorophenoxy)-propionitrile $C_9H_7Cl_2NO$ [(216.1] are obtained. Bp$_{0.2}$: 85° C. $[\alpha]_D^{20} = -76.6°$ (undiluted)

(−)-2-[1-(2,6-dichlorophenoxy)-ethyl]-1,3-diazacyclopent-2-ene 20.0 g (=0.0925 mols) of (−)-2-(2,6-dichlorophenoxy)-propionitrile are converted into (−)-2-(2,6-dichlorophenoxy)-propionimido acid ethylester-hydrochloride at 0° C. with 4.3 g (=0.0925 mols) of ethanol in 50 ml of absolute chloroform by introducing hydrogen chloride. This product is then dissolved in 20 ml of ethanol after removing the solvent under vacuum at 20° C. and is cyclised with 6.0 g ( 0.1 mol) of 1,2-diaminoethane into (−)-2-[1-(2,6-dichlorophenoxy)-ethyl]-1,3-diazacyclopent-2-ene $C_{11}H_{12}Cl_2H_nO$ [259.1]. After working up, 16 g of product are obtained. Mp. 127°–128° C.: $[\alpha]_D^{20} = -80.7°$ (c=1/ethanol).

(−)-2-[1-(2,6-dichlorophenoxy)-ethyl]-1,3-diazacyclopent-2-ene hydrochloride 4.0 g of (−)-2-[1-(2,6-dichlorophenoxy)-ethyl]-1,3-diazacyclopent-2-ene are dissolved in 16 ml of propan- 2-ol and are mixed with 16 ml of a saturated solution of hydrogen chloride in propan-2-ol. 3.3 g of (−)-2-[1-(2,6-dichlorophenoxy)-ethyl]-1,3-diazacyclopent-2-ene hydrochloride $C_{11}H_{12}Cl_2N_2O$ HCl [295.6] are obtained, Mp. 228°–229° C. $[\alpha]_D^{20} = -33.4°$ (c=1/ethanol).

EXAMPLE 3

Pharmaceutical formulation of the compound according to the present invention.

150 mg tablets containing 0.1 mg of active substance
(−)-2-[1-(2,6-dichlorophenoxy)-ethyl]-1,3-diazacyclopent-2-ene hydrochloride: 0.006 kg
Avicel: 7.584 kg
Citric acid: 1.200 kg
Aerosil: 0.120 kg
Magnesium stearate: 0.090 kg

What we claim is:

1. Process for producing (−)-2-[1-(2,6-dichlorophenoxy)-ethyl]-1,3-diazacyclopent-2-ene or a pharmaceutically acceptable acid addition salt thereof by subjecting a (−)-2-hydroxypropionic acid-$C_{1-4}$-alkyl ester to reaction with excess thionylchloride in the presence of catalytic quantities of dimethylformamide, subjecting the resulting (+)-2chloropropionic acid-$C_{1-4}$-alkyl ester to reaction with at least equimolar amounts of 2,6-dichlorophenol in an organic solvent in the presence of a base at a temperature ranging from 60° to 150° C., subjecting the resulting (−)-2-(2,6-dichlorophenoxy)-propionic acid-$C_{1-4}$-alkyl ester to reaction with a large excess of ethylene diamine at room temperature, subjecting the resulting (−)-2-(2,6-dichlorophenoxy)-propionic acid-N-(2-aminoethyl)-amide to dehydration with a titanium tetrachloride/tetrahydrofurane complex in an inert solvent in the presence of 4-dimethylamino pyridine at a temperature ranging from 0° to 30° C. and, if desired, converting the resulting (−)-2-(2,6-dichlorophenoxy)-ethyl]-1,3-diazacyclopent-2-ene into a physiologically acceptable acid addition salt thereof.

2. Process according to claim 1 wherein the reaction of the (+)-2-chloropropionic acid-$C_{1-4}$-alkyl ester with 2,6-dichlorophenol is effected at a temperature ranging from 80° to 100° C.

* * * * *